US012741028B2

(12) United States Patent
Kumagai et al.

(10) Patent No.: US 12,741,028 B2
(45) Date of Patent: Sep. 22, 2026

(54) CELLULOSE COMPOSITION AND TABLET

(71) Applicant: ASAHI KASEI KABUSHIKI KAISHA, Tokyo (JP)

(72) Inventors: Tadahiro Kumagai, Tokyo (JP); Yuji Hayashi, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 1133 days.

(21) Appl. No.: 17/767,996

(22) PCT Filed: Nov. 7, 2019

(86) PCT No.: PCT/JP2019/043583

§ 371 (c)(1),
(2) Date: Apr. 11, 2022

(87) PCT Pub. No.: WO2021/090422

PCT Pub. Date: May 14, 2021

(65) Prior Publication Data

US 2023/0055674 A1 Feb. 23, 2023

(51) Int. Cl.

| | |
|---|---|
| ***A61K 47/38*** | (2006.01) |
| ***A61K 9/20*** | (2006.01) |
| ***A61K 47/14*** | (2017.01) |
| ***A61K 47/26*** | (2006.01) |

(52) U.S. Cl.

CPC ............ *A61K 47/38* (2013.01); *A61K 9/2018* (2013.01); *A61K 9/2054* (2013.01); *A61K 47/14* (2013.01); *A61K 47/26* (2013.01)

(58) Field of Classification Search

CPC .... A61K 47/38; A61K 9/2018; A61K 9/2054; A61K 47/14; A61K 47/26

See application file for complete search history.

(56) References Cited

U.S. PATENT DOCUMENTS

| | | | |
|---|---|---|---|
| 2008/0295985 A1 | 12/2008 | Moncla et al. | |
| 2009/0232892 A1 | 9/2009 | Yamasaki et al. | |
| 2010/0247665 A1* | 9/2010 | Takahashi .............. | A61K 47/38 424/499 |
| 2015/0110900 A1 | 4/2015 | Obae et al. | |
| 2015/0150804 A1 | 6/2015 | Obae et al. | |
| 2017/0275385 A1* | 9/2017 | Capanema ........... | C09J 197/005 |
| 2019/0008749 A1 | 1/2019 | Harris et al. | |

FOREIGN PATENT DOCUMENTS

| | | |
|---|---|---|
| JP | 57-195101 | 11/1982 |
| JP | 11-217401 | 8/1999 |
| JP | 2004-175796 | 6/2004 |
| JP | 2006-061038 | 3/2006 |
| JP | 2009-167134 | 7/2009 |
| JP | 2010-200720 | 9/2010 |
| JP | 2010-215556 | 9/2010 |
| JP | 5001847 | 8/2012 |
| JP | 2013-527876 | 7/2013 |
| JP | 2016-540003 | 12/2016 |
| RU | 2008128835 | 1/2010 |
| WO | 2011/141876 | 11/2011 |
| WO | 2013/180246 | 12/2013 |
| WO | 2013/180248 | 12/2013 |
| WO | 2013/180249 | 12/2013 |
| WO | 2015/086467 | 6/2015 |
| WO | 2018/021265 | 2/2018 |

OTHER PUBLICATIONS

Horio, Takehiko, Masatoshi Yasuda, and Shuji Matsusaka. "Effect of particle shape on powder flowability of microcrystalline cellulose as determined using the vibration shear tube method." International journal of pharmaceutics 473.1-2 (2014): 572-578. (Year: 2014).*
Zarmpi, Panagiota, et al. "Biopharmaceutical aspects and implications of excipient variability in drug product performance." European Journal of Pharmaceutics and Biopharmaceutics 111 (2017): 1-15. (Year: 2017).*
Cello-oligosaccharide webpage from TCI Chemical <www.tcichemicals.com/US/en/product/glyco-chem/topics/natural_oligosaccharides>, obtained on Jul. 25, 2025 (Year: 2025).*
Xiao, Shaoliang, et al. "Fabrication and characterization of nanofibrillated cellulose and its aerogels from natural pine needles." Carbohydrate polymers 119 (2015): 202-209. (Year: 2015).*
"The Japanese Pharmacopoeia Seventeenth edition." English version (2016). (Year: 2016).*
Kharkevich DA, Pharmacology, Moscow, Medicine, 1987, p. 48, with corresponding English translation.
Ishchenko V.I., Industrial Technology of Medicines, 2nd ed., Vitebsk 2012, pp. 173, 174, with corresponding English translation.
Chueshov V.I., Gladukh E.V., Saiko I.V. and others., Technology of drugs for industrial production, textbook for students of higher educational institutions: translation from the text: at 2 hours P1.—Vinnitsa: Nova Kniga, 2014, pp. 198-199, with corresponding English translation.
"Internet source Extrusion", found on the Internet on Aug. 28, 2018, link to the source https://web.archive.org/web/20180828055103/https://ptl.by/index.pl?act=PRODUCT&id=21, with corresponding English translation.
International Search Report issued in International Patent Application No. PCT/JP2019/043583, dated Dec. 10, 2019, along with an English translation thereof.
Written Opinion of the International Searching Authority issued in International Application No. PCT/JP2019/043583, dated Dec. 10, 2019, along with an English translation thereof.
European search report dated Oct. 19, 2022 issued in European patent application No. 19951364.9.
Billes Elise et al., "Water-soluble cellulose oligomer production by chemical and enzymatic synthesis: a mini-review", Polymer International, vol. 66, No. 9, Jun. 15, 2017.

* cited by examiner

*Primary Examiner* — Scarlett Y Goon
*Assistant Examiner* — David H Cho
(74) *Attorney, Agent, or Firm* — Greenblum & Bernstein, P.L.C.

(57) ABSTRACT

A cellulose composition containing cellulose and cellooligosaccharides from trisaccharides to heptasaccharides, wherein the cellooligosaccharide content per 5 g of the cellulose composition is at least 1.5 mg but not more than 9.0 mg. A tablet contains the cellulose composition and at least one active component.

12 Claims, No Drawings

CELLULOSE COMPOSITION AND TABLET

TECHNICAL FIELD

The present invention relates to a cellulose composition and a tablet.

BACKGROUND ART

Tableting of pharmaceuticals offers the advantages of high productivity and ease of handling during transport and use. During tableting, because many active component raw materials cannot be molded even when compressed, excipients are added to enable tableting, with these excipients requiring favorable moldability, flowability and disintegrability. Cellulose is widely used as an excipient.

Patent Document 1 discloses a cellulose powder having an average degree of polymerization of at least 100 but not more than 350, a weight-average particle size of greater than 30 μm but not more than 250 μm, an apparent specific volume of at least 2 $cm^3/g$ but less than 15 $cm^3/g$, and a particle size distribution sharpness of at least 1.5 but not more than 2.9. It is disclosed that using this cellulose powder provides excellent compression moldability, and has the effects of enabling traditional Chinese medicine components having high levels of stickiness and hygroscopicity and other components having adhesiveness to be retained in a uniform manner, providing a sharper particle size distribution for the granules due to the sharp particle size distribution of the cellulose powder, offering a shortened disintegration time, and imparting more stable disintegrability over a long period of time.

On the other hand, when a cellulose powder of conventional technology is used, in order to ensure uniformity of active component content in each tablet, the raw material mixing time tends to require lengthening, and the reduction in tablet hardness accompanying this lengthening of mixing time can become problematic. However, satisfactory mixing is essential to prevent maldistribution of the active component, and preventing any reduction in the tablet hardness caused by lengthening of the mixing time, while simultaneously preventing any deterioration in content uniformity has proven difficult.

PRIOR ART LITERATURE

Patent Document

Patent Document 1: International Patent Publication No. WO 2013/180248

SUMMARY OF INVENTION

Problems to be Solved by the Invention

The present invention has been developed in light of the above circumstances, and provides a cellulose composition having favorable hardness and good suppression of both deviation in the active component content and tableting failure during molding, as well as a tablet containing the cellulose composition.

Means for Solving the Problems

In other words, the present invention includes the following aspects.

(1) A cellulose composition comprising cellulose and cellooligosaccharides from trisaccharides to heptasaccharides, wherein the cellooligosaccharide content per 5 g of the cellulose composition is at least 1.5 mg but not more than 9.0 mg.

(2) The cellulose composition according to (1), wherein the water-soluble substance content per 5 g of the cellulose composition is at least 2.5 mg but not more than 12.5 mg.

(3) The cellulose composition according to (2), wherein the proportion of the cellooligosaccharides relative to the water-soluble substances is at least 47% by mass but not more than 67% by mass.

(4) The cellulose composition according to any one of (1) to (3), wherein the cellulose composition is a powder, and the average particle size of the powder is at least 10 μm but not more than 200 μm.

(5) The cellulose composition according to (4), wherein the aspect ratio L/D of the powder is at least 1.8 but not more than 4.0.

(6) A tablet comprising the cellulose composition of any one of (1) to (5), and at least one active component.

(7) The tablet according to (6), wherein the lubricant content, relative to the total mass of the tablet, is at least 0.3% by mass but not more than 5% by mass.

(8) The tablet according to (7), wherein the lubricant is at least one substance selected from the group consisting of fatty acid metal salts, fatty acid esters and fatty acid ester metal salts.

(9) The tablet according to (7) or (8), wherein the lubricant is at least one substance selected from the group consisting of magnesium stearate, calcium stearate, sodium stearyl fumarate, stearic acid, sucrose fatty acid esters, and talc.

(10) The tablet according to any one of (6) to (9), wherein the active component content, relative to the total mass of the tablet, is at least 0.01% by mass but less than 50% by mass.

Effects of the Invention

By using a cellulose composition of an aspect described above, a cellulose composition can be provided that has favorable hardness and good suppression of both deviation in the active component content and tableting failure during molding. A tablet of an aspect described above comprises the cellulose composition, and exhibits favorable hardness and good suppression of both deviation in the active component content and tableting failure during molding.

EMBODIMENTS FOR CARRYING OUT THE INVENTION

Embodiments for implementing the present invention (hereafter referred to as simply "embodiments of the present invention") are described below in detail. The present invention is not limited to the following embodiments, and various modifications may be made within the scope of the present invention.

<Cellulose Composition>

A cellulose composition of an embodiment of the present invention contains cellulose and cellooligosaccharides from trisaccharides to heptasaccharides (hereafter sometimes abbreviated as "cellooligosaccharides (3 to 7)"). The cellooligosaccharide (3 to 7) content per 5 g of the cellulose composition is at least 1.5 mg but not more than 9.0 mg, and is preferably at least 2.0 mg but not more than 8.0 mg, more preferably at least 3.0 mg but not more than 7.5 mg, even more preferably at least 4.0 mg but not more than 7.5 mg, and particularly preferably at least 5.0 mg but not more than 7.5 mg.

By ensuring that the cellooligosaccharide (3 to 7) content per 5 g of the cellulose composition falls within the above range, any reduction in tablet hardness accompanying lengthening of the mixing time can be effectively prevented. In those cases where the cellulose composition is a powder, it is preferable that each single particle contains cellulose and the cellooligosaccharides (3 to 7).

Conventionally, from the viewpoint of quality assurance, pharmaceutical additives and food additives have required substances of high purity, and conventional cellulose powders used as pharmaceutical additives are formed from pure cellulose with an extremely high degree of purity. In contrast, the cellulose composition of an embodiment of the present invention may contain a specified amount of the types of water-soluble substances that have conventionally been removed. These water-soluble substances are composed mainly of monosaccharides such as glucose and sorbitol, and cellooligosaccharides such as cellobiose, cellotriose, cellotetraose, cellopentaose, cellohexaose and celloheptaose. Among these constituent components, it is important that the total amount of cellotriose, cellotetraose, cellopentaose, cellohexaose and celloheptaose (hereafter, these components are jointly referred to as the "cellooligosaccharides (3 to 7)" falls within a specific range. When mixing the raw materials of a tablet, it is thought that abrasion between particles and the generation of powders and the like result in a deterioration in the binding properties between the particles, causing a reduction in the tablet hardness, but it is thought that by using a cellulose composition for which the cellooligosaccharide content is within the range described above, the binding between particles can be appropriately enhanced, enabling any reduction in the tablet hardness to be effectively suppressed.

As illustrated in the examples described below, the cellooligosaccharide (3 to 7) content within 5 g of the cellulose composition is measured by liquid chromatography/mass spectrometry (LC/MS). In those cases where the composition contains other components that are likely to overlap with the peaks attributable to the cellooligosaccharides (3 to 7), the conditions for the liquid chromatography are first adjusted appropriately to ensure that peak separation is possible. If peak separation is impossible, then within the mass spectrometry, an extracted ion chromatogram of the base peak ions attributable to the cellooligosaccharides (3 to 7) can be used to determine the peak surface area attributable to the cellooligosaccharides (3 to 7).

The cellooligosaccharide (3 to 7) content within the cellulose composition can be adjusted, for example, by adding the cellooligosaccharides (3 to 7) during production of the cellulose composition. Commercially available products may be procured and used as the cellooligosaccharides (3 to 7), or the cellooligosaccharides (3 to 7) can be obtained by appropriate hydrolysis of a natural cellulose material such as pulp, and then extraction, separation and purification of the desired cellooligosaccharides from the obtained hydrolysate.

In the cellulose composition of an embodiment of the present invention, the water-soluble substance content per 5 g of the cellulose composition is preferably at least 0.5 mg but not more than 12.5 mg, more preferably at least 2.5 mg but not more than 12.5 mg, even more preferably at least 5.0 mg but not more than 12.5 mg, and particularly preferably at least 6.0 mg but not more than 12.0 mg.

By ensuring that the water-soluble substance content falls within the above range, the tablet hardness can be adjusted to a more favorable level. Further, reactivity with the active component(s) can be effectively suppressed.

As described below in the examples, the water-soluble substance content can be measured in accordance with the crystalline cellulose purity test (2) method described in the 17th edition of the Japanese Pharmacopoeia, thus enabling measurement of the water-soluble substance content per 5 g of the cellulose composition.

In the cellulose composition of an embodiment of the present invention, the proportion of the cellooligosaccharides (3 to 7) relative to all the water-soluble substances is at least 47% by mass but not more than 68% by mass, preferably at least 50% by mass but not more than 67% by mass, even more preferably at least 55% by mass but not more than 66% by mass, and particularly preferably at least 60% by mass but not more than 65% by mass.

By ensuring that the proportion of the cellooligosaccharides (3 to 7) relative to the water-soluble substances falls within the above range, any reduction in hardness due to lengthening of the mixing time can be effectively suppressed. Further, reactivity with the active component(s) can also be suppressed to a low level, meaning the storage stability is also more favorable.

The water-soluble substances in the cellulose composition of an embodiment of the present invention can be measured using the method described in the examples below.

<Form of Cellulose Composition>

The cellulose composition according to an embodiment of the present invention preferably exists in the form of a powder, granules, a paste, or a wet cake. From the viewpoint of the handling properties, a cellulose powder is preferred. A cellulose powder is typically described as a crystalline cellulose or a powdered cellulose or the like, and can be used favorably as a pharmaceutical additive or food additive. Known examples of crystalline celluloses include the microcrystalline cellulose specified by the Joint FAO/WHO Expert Committee on Food Additives (JECFA), the microcrystalline cellulose disclosed in the 8th edition of the Japanese Standards of Food Additives, the crystalline cellulose disclosed in the Japanese Pharmacopoeia (17th edition), and crystalline celluloses disclosed in the United States Pharmacopoeia and the European Pharmacopoeia.

From the viewpoint of achieving a favorable balance between moldability, flowability and disintegrability, the average degree of polymerization of the cellulose in the cellulose composition is preferably not more than 400, and is more preferably 350 or lower. The lower limit for the average degree of polymerization is preferably at least 100. The average degree of polymerization of the cellulose can be measured using the copper ethylenediamine solution viscosity method disclosed in the crystalline cellulose confirmation test (3) or the powdered cellulose confirmation test (3) described in the Japanese Pharmacopoeia.

<Preferred Form for Cellulose Powder>

In those cases where the cellulose composition of an embodiment of the present invention is a powder, the average particle size of the powder is at least 10 μm but not more than 200 μm, and is preferably at least 15 μm but not more than 100 μm, more preferably at least 20 μm but not more than 90 μm, even more preferably at least 30 μm but not more than 70 μm, and particularly preferably at least 40 μm but not more than 60 μm.

By ensuring that the average particle size is not higher than the above upper limit, the cellulose powder can be mixed more uniformly with active components such as drugs, and the moldability also improves. In particular, provided the average particle size is at least 20 μm, the flowability of the powder tends to be more favorable.

The average particle size of the cellulose powder is the particle size at a cumulative volume of 50% measured using a laser diffraction particle size distribution meter (LA950 V2 (brand name), manufactured by Horiba, Ltd.).

In those cases where the cellulose composition of an embodiment of the present invention is a powder, the loose bulk density is preferably at least 0.11 g/mL but not more than 0.35 g/mL, more preferably at least 0.13 g/mL but not more than 0.33 g/mL, and even more preferably at least 0.18 g/mL but not more than 0.31 g/mL.

By ensuring that the loose bulk density is at least as high as the above lower limit, the compression moldability can be improved. On the other hand, by ensuring that the loose bulk density is not more than the above upper limit, the packing properties can be improved.

The loose bulk density can be measured using the method disclosed in the examples described below.

In those cases where the cellulose composition of an embodiment of the present invention is a powder, the packed bulk density is preferably at least 0.25 g/mL but not more than 0.50 g/mL, more preferably at least 0.30 g/mL but not more than 0.45 g/mL, and even more preferably at least 0.32 g/mL but not more than 0.42 g/mL.

By ensuring that the packed bulk density is at least as high as the above lower limit, the powder can be mixed more uniformly with active components such as drugs, and the handling properties also improve. On the other hand, by ensuring that the packed bulk density is not more than the above upper limit, any maldistribution resulting from the density difference from the active component(s) or other additives can be more effectively suppressed.

The packed bulk density can be measured using the method disclosed in the examples described below.

Further, in those cases where the loose bulk density and the packed bulk density simultaneously satisfy the ranges described above, the tablets obtained by compression molding tend to exhibit superior moldability and disintegrability.

In those cases where the cellulose composition of an embodiment of the present invention is a powder, the compressibility is preferably at least 25% but not more than 58%, more preferably at least 30% but not more than 58%, and even more preferably at least 35% but not more than 58%.

Provided the compressibility falls within the above range, the flowability of the cellulose powder itself can be improved, and maldistribution of components in the powder can be more effectively suppressed.

The compressibility can be calculated using the method disclosed in the examples described below.

In those cases where the cellulose composition of an embodiment of the present invention is a powder, the primary particle-equivalent average particle size (hereafter sometimes abbreviated as the "primary particle-equivalent particle size") is preferably at least 15 μm but not more than 30 μm, more preferably at least 16 μm but not more than 29 μm, and even more preferably at least 16 μm but not more than 27 μm.

By ensuring that the primary particle-equivalent particle size falls within the above range, the cellulose powder can be mixed more uniformly with active components such as drugs, and the disintegrability when formed as a tablet becomes more favorable.

A primary particle refers to a unit particle, and an aggregate or agglomerate of primary particles is termed a secondary particle. Secondary particle aggregates can be broken down and retuned to primary particles by dispersion in water. The primary particle-equivalent average particle size can be measured using the method disclosed in the examples described below.

In those cases where the cellulose composition of an embodiment of the present invention is a powder, the ratio of the long axis relative to the short axis of the cellulose particles, namely, the aspect ratio (L/D), is preferably at least 1.8 but not more than 4.0, more preferably at least 2.1 but not more than 3.5, and even more preferably at least 2.2 but not more than 3.1.

By ensuring that the aspect ratio falls within the above range, the mixability with active components is also favorable, and the degree of intertwining of elongated particles is also appropriate, resulting in an excellent balance between moldability and disintegrability.

The aspect ratio (L/D) can be measured using the method disclosed in the examples described below.

<Method for Producing Cellulose Composition>

One example of a method for producing the cellulose composition of an embodiment of the present invention is described below.

The cellulose composition of an embodiment of the present invention can be obtained, for example, using a method that includes a step of dispersing a hydrolyzed natural cellulose-based substance in a suitable solvent to obtain a cellulose aqueous dispersion, and a step of drying the cellulose aqueous dispersion. There are no particular limitations on the solid fraction concentration of the cellulose aqueous dispersion, and the concentration may be set, for example, to at least 1% by mass but not more than 30% by mass. In such cases, the solid fraction containing the hydrolyzed cellulose-based substance may be isolated from the hydrolysis reaction solution obtained from the hydrolysis treatment, and a dispersion prepared by dispersing this solid fraction in a suitable solvent may then be dried. Further, in order to ensure that the cellooligosaccharide (3 to 7) content in the cellulose composition falls within the specified range, cellooligosaccharides may be added to and mixed with the cellulose dispersion before drying is conducted. Furthermore, in those cases where the hydrolysis solution itself forms a cellulose dispersion, this dispersion may be dried directly.

The natural cellulose-based substance may be plant-based or animal-based, and examples include natural material-derived fibrous substances containing cellulose such as timber, bamboo, cotton, ramie, hoya, bagasse, kenaf and bacteria cellulose, although the substance preferably has a cellulose 1 crystal structure. One of the above natural cellulose-based substances may be used as the raw material, or a mixture of two or more substances may be used. Further, it is preferable that the substance is used in the form of a purified pulp, but there are no particular limitations on the pulp purification method used, and any pulp such as dissolving pulp, kraft pulp or NBKP pulp may be used.

In the above production method, water is preferred as the solvent used when dispersing the solid fraction containing the natural cellulose-based substance in a suitable solvent, but any industrially used solvent may be used without any particular limitations, and for example, organic solvents may also be used. Examples of such organic solvents include alcohols such as methanol, ethanol, isopropyl alcohol, butyl alcohol, 2-methylbutyl alcohol and benzyl alcohol; hydrocarbons such as pentane, hexane, heptane and cyclohexane; and ketones such as acetone and methyl ethyl ketone. Organic solvents used in pharmaceuticals are particularly preferred, and examples of such solvents include those classified as solvents in "Pharmaceutical Excipients Directory 2016" (published by Yakuji Nippo, Ltd.). Either water or a single organic solvent may be used alone, or a mixture of two or more solvents may be used, and the substance may also be first dispersed in one solvent, and following removal of that solvent, subsequently dispersed in another solvent.

For example, pulp fibers having an average width of at least 2 μm but not more than 30 μm and an average thickness of at least 0.5 μm but not more than 5 μm may be hydrolyzed while agitating with a stirrer under pressure in hydrochloric acid of at least 0.05% by mass but not more than 1.5% by mass at a temperature of at least 70° C. but not more than 140° C.

The degree of progression of the hydrolysis can be controlled by adjusting the motor output of the stirrer (P: units W) and the stirring volume (L: units L). For example, by adjusting the P/V value represented by the formula shown below, the average particle size of the finally obtained cellulose particles can be controlled to a value of not more than 200 μm.

$$P/V(W/L) = [\text{Actual power output of stirrer motor } (W)]/[\text{Stirring volume } (L)]$$

There are no particular limitations on the drying method used when drying the cellulose aqueous dispersion to obtain a cellulose composition. For example, freeze drying, spray drying, drum drying, rack drying, convection drying, or vacuum drying may be used, and either a single drying method or a combination of two or more drying methods may be used. In the case of spray drying, the spraying method may employ any of disk spraying, pressurized nozzle spraying, pressurized two-fluid nozzle spraying and pressurized four-fluid nozzle spraying, and either one of these methods or a combination of two or more methods may be used.

In the case of the spray drying mentioned above, a trace amount of a water-soluble polymer or surfactant may be added for the purpose of lowering the surface tension of the dispersion, and a foaming agent or gas may be added to the dispersion for the purpose of accelerating the solvent vaporization rate.

By controlling the acid concentration and the stirring conditions during preparation of the cellulose aqueous dispersion, a cellulose aqueous dispersion can be obtained which contains cellulose dispersed particles with an average particle size that satisfies a specific size, water-soluble substances which are incorporated within the cellulose particles in an amount that falls within a specific range, and cellooligosaccharides (3 to 7) which are incorporated within the water-soluble substances in an amount that falls within a specific range, and by also adjusting the solid fraction concentration of the cellulose aqueous dispersion and the drying conditions when drying this cellulose aqueous dispersion, the average particle size and compressibility of the obtained cellulose composition can be controlled. For example, when the drying of the cellulose aqueous dispersion is conducted by disk spray drying, by ensuring that the stirring power when preparing the cellulose aqueous dispersion falls within the specified range, and that the conditions for the solid fraction concentration of the cellulose aqueous dispersion and the rotational rate for the disk spray drying during the spray drying process satisfy the specified ranges, a cellulose composition for which the average particle size and the compressibility fall within the prescribed ranges can be obtained.

Furthermore, as disclosed in the following examples, a cellulose composition for which the cellooligosaccharide (3 to 7) content falls within the specified range may be obtained by adding and mixing cellooligosaccharides with the cellulose aqueous dispersion, and then drying the resulting dispersion.

Even in those cases where the average particle size of the cellulose composition following drying is greater than 200 μm, the average particle size can be adjusted to a value of at least 10 μm but not more than 200 μm by supplying the composition to a grinding step described below.

The grinding step can be conducted by grinding the dried cellulose composition with a grinder such as an Ultra Centrifugal Mill (ZM-200, manufactured by Retsch GmbH), a Jet Mill (STJ-200, manufactured by Seishin Enterprise Co., Ltd.), a Hammer Mill (H-12, manufactured by Hosokawa Micron Corporation, or HM-600, manufactured by Nara Machinery Co., Ltd.), a Bantam Mill (AP-B, manufactured by Hosokawa Micron Corporation), a Pin Mill (160Z, manufactured by Powrex Corporation), a Feather Mill (FM, manufactured by Hosokawa Micron Corporation), a Flash Mill (FL-250N, manufactured by Dalton Corporation), a Ball Mill (Emax, manufactured by Retsch GmbH), a Vibrating Ball Mill (2C, manufactured by TRU Tech Systems Inc.), or a Screen Mill in which the composition is passed through a screen (U30, manufactured by Powrex Corporation). In particular, the Jet Mill (STJ-200, manufactured by Seishin Enterprise Co., Ltd.) is a convection-type grinder in which grinding is conducted while the particles are caused to collide with one another under high air pressure, thus facilitating the breakup of secondary particles into primary particles, and is consequently preferred.

Among the grinding conditions for the Jet Mill grinder, the amount of powder supplied and the grinding pressure are important, and the supply amount when using the Jet Mill grinder (STJ-200, manufactured by Seishin Enterprise Co., Ltd.) is preferably at least 10 kg/hour but not more than 20 kg/hour, and more preferably at least 15 kg/hour but not more than 20 kg/hour. Further, the grinding pressure is preferably at least 0.15 MPa but not more than 0.70 MPa, and more preferably at least 0.30 MPa but not more than 0.50 MPa. Provided the supply amount of the powder and the grinding pressure satisfy the above ranges, the average particle size tends to be more easily adjusted to a value within the desired range of at least 10 μm but not more than 200 μm.

Even in those cases where the average particle size of the dried cellulose powder is less than 100 μm, by subjecting the cellulose powder to a granulation method such as stirring granulation or fluidized bed granulation, the average particle size can be adjusted to a value within the desired range from at least 100 μm to not more than about 200 μm.

<Usage Applications>

By blending the cellulose composition of an embodiment of the present invention with a composition containing an active component, tablets can be obtained which have favorable hardness and good suppression of both reduction in the tablet hardness caused by lengthening of the mixing time and deviation in the active component content. These effects are particularly marked in tablets for which the active component content is less than 50% by mass.

In the following description, when discussing production of a tablet, the mixtures obtained by mixing at least one active component, the cellulose composition of an embodiment of the present invention and any other optional additives is referred to as a "tablet mixture".

The blend proportion of the cellulose composition described above in the tablet mixture, expressed relative to the total mass of the obtained tablet, is normally at least 1% by mass but not more than 90% by mass, preferably at least 1% by mass but not more than 50% by mass, more preferably at least 1% by mass but not more than 30% by mass, even more preferably at least 3% by mass but not more than 20% by mass, and particularly preferably at least 5% by mass but not more than 15% by mass.

[Active Component]

Examples of components that are ideal as the active component for inclusion in the tablet mixture are described below.

The pharmaceutical medicinal component is preferably an active component of an orally administered pharmaceutical. Examples of orally administered pharmaceuticals include antipyretic analgesic anti-inflammatory drugs, sedative hypnotic drugs, anti-drowsiness drugs, anti-vertiginous drugs, pediatric analgesics, stomachic drugs, antacids, digestive drugs, cardiotonic drugs, arrhythmia drugs, antihypertensive drugs, vasodilators, diuretics, antiulcer drugs, intestinal regulators, osteoporosis treatments, antitussive drugs, anti-asthmatic drugs, antibacterial agents, pollakiuria improvement agents, nourishing tonics, and vitamins. Any of these medicinal components may be used individually, or a combination of two or more components may be used.

Specific examples of medicinal components include aspirin, aspirin aluminum, acetaminophen, ethenzamide, sasapyrine, salicylamide, lactylphenetidine, isothipendyl hydrochloride, diphenylpyraline hydrochloride, diphenhydramine hydrochloride, difeterol hydrochloride, triprolidine hydrochloride, tripelennamine hydrochloride, thonzylamine hydrochloride, fenethazine hydrochloride, methdilazine hydrochloride, diphenhydramine salicylate, carbinoxamine diphenyldisulfonate, alimemazine tartrate, diphenhydramine tannate, diphenylpyraline teoclate, mebhydrolin napadisilate, promethazine methylenedisalicylate, carbinoxamine maleate, chlorpheniramine dl-maleate, chlorpheniramine d-maleate, difeterol phosphate, alloclamide hydrochloride, cloperastine hydrochloride, pentoxyverine citrate (carbetapentane citrate), tipepidine citrate, sodium dibunate, dextromethorphan hydrobromide, dextromethorphan phenolphthalate, tipepidine hibenzate, cloperastine fendizoate, codeine phosphate, dihydrocodeine phosphate, noscapine hydrochloride, noscapine, dl-methylephedrine hydrochloride, dl-methylephedrine saccharin salt, potassium guaiacolsulfonate, guaifenesin, caffeine sodium benzoate, caffeine, anhydrous caffeine, vitamin B1 and derivatives and salts thereof, vitamin B2 and derivatives and salts thereof, vitamin C and derivatives and salts thereof, hesperidin and derivatives and salts thereof, vitamin B6 and derivatives and salts thereof, nicotinamide, calcium pantothenate, aminoacetic acid, magnesium silicate, synthetic aluminum silicate, synthetic hydrotalcite, magnesium oxide, dihydroxyalurninurn aminoacetate (aluminum glycinate), aluminum hydroxide gel, dried aluminum hydroxide gel, mixed dry gel of aluminum hydroxide and magnesium carbonate, co-precipitated product of aluminum hydroxide and sodium hydrogen carbonate, co-precipitated product of aluminum hydroxide, calcium carbonate and magnesium carbonate, co-precipitated product of magnesium hydroxide and aluminum potassium sulfate, magnesium carbonate, magnesium aluminometasilicate, ranitidine hydrochloride, cimetidine, famotidine, naproxen, diclofenac sodium, piroxicum, azulene, indomethacin, ketoprofen, ibuprofen, diphenidol hydrochloride, diphenylpyraline hydrochloride, diphenhydramine hydrochloride, promethazine hydrochloride, meclizine hydrochloride, dimenhydrinate, diphenhydramine tannate, phenethazine tannate, diphenylpyraline teoclate, diphenhydramine fumarate, promethazine methylenedisalicylate, scopolamine hydrobromide, oxyphencycli mine hydrochloride, dicyclomine hydrochloride, methixene hydrochloride, methylatropine bromide, methylanisotropine bromide, methylscopolamine bromide, methyl-1-hyoscyamine bromide, methylbenactyzium bromide, belladonna extract, isopropamide iodide, diphenylpiperidinomethyldioxolan iodide, papaverine hydrochloride, aminobenzoic acid, cesium oxalate, ethyl piperidylacetylaminobenzoate, aminophylline, diprophylline, theophylline, sodium hydrogen carbonate, fursultiamine, isosorbide mononitrate, ephedrine, cephalexin, ampicillin, sulfisoxazole, sucralfate, allylisopropylacetylurea, bromvalerylurea; as well as ephedra, nantenzitu, oohi, polygala root, glycyrrhiza, platycodon, plantago seed, plantago herb, senega, fritillaria, fennel, phellodendron bark, coptis rhizome, curcuma zedoaria, chamomile, cassia bark, gentian, oriental bezoar, animal bile (including bear bile), syazin, ginger, atractylodes lancea rhizome, clove, citrus unshiu, atractylodes rhizome, ziryuu, panax rhizome, ginseng, Japanese valerian, moutan bark, zanthoxylum, and extracts of these plants; and pharmaceutical medicinal components disclosed in the "Japanese Pharmacopoeia", "Japanese Pharmaceutical Codex", "United States Pharmacopoeia (USP)", "National Formulary (NF)" and "European Pharmacopoeia (EP)", such as insulin, vasopressin, interferon, urokinase, serratiopeptidase and somatostatin. A single substance selected from among the above substances may be used alone, or a combination of two or more substances may be used.

There are no particular limitations on health food active components that may be used, provided the component is added for the purpose of enhancing health, and examples include green juice powder, aglycone, agaricus, ashwagandha, astaxanthin, acerola, amino acids (such as valine, leucine, isoleucine, lysine, methionine, phenylalanine, threonine, tryptophan, histidine, cystine, tyrosine, arginine, alanine, aspartic acid, seaweed powder, glutamine, glutamic acid, glycine, proline, and serine), alginic acid, gingko leaf extract, sardine peptide, turmeric, uronic acid, echinacea, eleuthero, oligosaccharides, oleic acid, nuclear proteins, bonito peptide, catechin, potassium, calcium, carotenoids, garcinia, L-carnitine, chitosan, conjugated linoleic acid, krantz aloe, gymnema sylvestre extract, citric acid, orthosiphon stamineus, glycerides, glycenol, glucagon, curcumin, glucosamine, L-glutamine, chlorella, cranberry extract, cat's claw, germanium, enzymes, ginseng extract, coenzyme Q10, collagen, collagen peptides, coleus forskolin, chondroitin, psyllium husk powder, hawthorn extract, saponin, lipids, L-cystine, perilla extract, citrimax, fatty acids, plant sterols, seed extracts, spirulina, squalane, white willow, ceramides, selenium, St. John's wort extract, soy isoflavone, soy saponin, soy peptide, soy lecithin, monosaccharides, proteins, chaste tree extract, iron, copper, docosahexaenoic acid, tocotrienol, natto kinase, bacillus natto culture extract, niacin sodium, nicotinic acid, disaccharides, lactic acid bacteria, garlic, saw plametto, sprouted rice, adlay extract, herb extracts, valerian extract, pantothenic acid, hyaluronic acid, biotin, chromium picolinate, vitamin A, vitamin A2, vitamin B1, vitamin B2, vitamin B6, vitamin B12, vitamin C, vitamin D, vitamin E, vitamin K, hydroxytyrosol, bifidus, beer yeast, fructooligosaccharides, flavonoids, butcher's broom extract, black cohosh, blueberry, prune extract, proanthocyanidin, proteins, propolis, bromelain, probiotics, phosphatidylcholine, phosphatidylserine, β-carotene, peptides, safflower extract, maitake extract, maca extract, magnesium, milk thistle, manganese, mitochondria, minerals, mucopolysaccharides, melatonin, fomes yucatensis, melilot extract powder, molybdenum, vegetable powders, folic acid, lactose, lycopene, linoleic acid, lipoic acid, phosphorus, lutein, lecithin, rosmarinic acid, royal jelly, DHA, and EPA.

The active component may be water-soluble, or may be sparingly water-soluble. The term "sparingly water-soluble" is defined in the 17th edition of the Japanese Pharmacopoeia as requiring 30 mL or more of water to dissolve 1 g of solute.

Examples of sparingly water-soluble solid active components include pharmaceutical medicinal components disclosed in the "Japanese Pharmacopoeia", "Japanese Pharmaceutical Codex", "USP", "NF" and "EP", including antipyretic analgesics, nervous system drugs, sedative hypnotic drugs, muscle relaxants, hypotensive agent and antihistamines such as acetaminophen, ibuprofen, benzoic acid, ethenzamide, caffeine, camphor, quinine, calcium gluconate, dimercaprol, sulfamine, theophylline, theobromine, riboflavin, mephenesin, phenobarbital, aminophylline, thioacetazone, quercetin, rutin, salicylic acid, theophylline sodium, pyrabital, quinine hydrochloride, irgapyrin, digitoxin, griseofulvin, and phenacetin; antibiotics such as acetylspiramycin, ampicillin, erythromycin, kitasamycin, chloramphenicol, triacetyloleandomycin, nystatin, and colistin sulfate; steroid hormones such as methyltestosterone, methylandrostenediol, progesterone, estradiol benzoate, ethinylestradiol, deoxycorticosterone acetate, cortisone acetate, hydrocortisone, hydrocortisone acetate, and prednisolone; non-steroidal estrogen hormones such as dienestrol, hexestrol, diethylstilbesterol, diethylstilbestrol dipropionate, and chlorotrianisene; and other fat-soluble vitamins and the like. A single substance selected from among the above substances may be used alone, or a combination of two or more substances may be used. if the substance is sparingly water-soluble, then regardless of the sublimability and degree of surface polarity, the effects of the present invention can be achieved by blending the active component with the tablet mixture.

The active component may also be a sparingly water-soluble oil or liquid. Examples of sparingly water-soluble oil or liquid components that may be used as active components include pharmaceutical medicinal components disclosed in the "Japanese Pharmacopoeia", "Japanese Pharmaceutical Codex", "USP", "NF" and "EP", including vitamins such as teprenone, indometacin farnesil, nienatetrenone, phytonadione, vitamin A oil, fenipentol, vitamin D and vitamin E, higher unsaturated fatty acids such as DHA (docosahexaenoic acid), EPA (eicosapentaenoic acid) and cod liver oil, coenzyme Q substances, and oil-soluble flavorings such as orange oil, lemon oil and peppermint oil. Vitamin E has various homologues and derivatives, but there are no particular limitations on the form of the vitamin, provided it is liquid at normal temperatures. Specific examples include dl-α-tocopherol, dl-α-tocopherol acetate, d-α-tocopherol, and d-α-tocopherol acetate. A single substance selected from among the above substances may be used alone, or a combination of two or more substances may be used.

The active component may also be a sparingly water-soluble semisolid active component. Among the various active components, examples of sparingly water-soluble semisolid active components include traditional Chinese medicines and crude drug extracts such as ziryuu, glycyrrhiza, cassia bark, Chinese peony, moutan bark, Japanese valerian, zanthoxylum, ginger, citrus unshiu, ephedra, nantenzitsu, oohi, polygala root, platycodon root, plantago seed, plantago herb, lycoris radiata bulb, senega, fritillaria bulb, fennel, phellodendron bark, coptis rhizome, curcuma zedoaria, chamomile, gentian, oriental bezoar, animal bile, syazin, ginger, atractylodes lancea rhizome, clove, citrus unshiu, atractylodes rhizome, panax rhizome, ginseng, kakkon-to, keishi-to, kousosan, saiko-keishi-to, sho-saiko-to, sho-seiryu-to, bakumondo-to, hange-koboku-to, and mao-to; as well as oyster meat extract, propolis and propolis extract, and coenzyme Q substances. A single substance selected from among the above substances may be used alone, or a combination of two or more substances may be used.

The active component may be a sublimable. Examples of such components include sublimable pharmaceutical medicinal components disclosed in the "Japanese Pharmacopoeia", "Japanese Pharmaceutical Codex", "USP", "NF" and "EP", including benzoic acid, ethenzamide, caffeine, camphor, salicylic acid, phenacetin and ibuprofen. A single substance selected from these substances may be used alone, or a combination of two or more substances may be used. In this description, there are no particular limitations on the sublimable component, provided it exhibits sublimability, and the component may be any one of a solid, a liquid or a semisolid at normal temperatures.

Further, medicinal components for which the maximum blend amount per tablet is small can be used particularly favorably as the active component.

Examples of medicinal components for which the maximum blend amount per tablet is small include the following medicinal components which are added in amounts of not more than 100 mg or not more than 10 mg.

Examples of medicinal components for which the maximum blend amount per tablet exceeds 100 mg include Abacavir, Acetazolamide, Acetylsalicylic acid, Aciclovir, Albendazole, Aliskiren Fumarate, Allopwinol, Amiodarone, Amodiaquine, Amoxicllin, Aprepitant, Artemether, Artesunate, Atazanavir, Calcium, Capecitabine, Carbamazepine, Carbidopa, Cefalexin, Cefixime, Celecoxib, Chloroquine, Ciprofloxacin, Clarithromycin, Clavulanate Potassium, Clopidogrel, Clozapine, Cycloserine, Darunavir, Darunavir ethanolate, Dasabuvir, Dasatinib, Deferasirox, Dihydroartemisinin piperaquine phosphate, Diloxanide, Efavirenz, Emtricitabine, Erlotinib hydrochloride, Ethambutol, Ethionamide, Famciclovir, Gefitinib, Griseofulvin, Hydroxycarbamide, Hydroxychloroquine, Ibuprofen, Imatinb, Irbesartan, Isoniazid, Lamivudine, Lamotrigine, Lanthanum carbonate hydrate, Ledipasvir, Levamisole, Levetiracetam, Levodopa, Levofloxacin, Linezolid, Lithium carbonate, Lopinavir, Lumefantrine, Mebendazole, Mefloquine, Mesna, Metformin, Methyldopa, Metronidazole, Morphine, Moxifloxacin, Nevirapine, Niclosamide, Nifurtimox, Ombitasvir, p-Aminosalicylic acid, Paracetamol, Paritaprevir, Penicillamine, Pentamidine, Phenoxymethylpenicillin, Pirfenidone, Praziquantel, Pyrantel, Pyrazinamide, Pyronaridine tetraphosphate, Quinine, Raltegravir, Ranitidine, Ribavirin, Rifampicin, Rifapentine, Sevelamer hydrochloride, Sofosbuvir, Sorafenib tosilate, Sulfadiazine, Sulfamethoxazole, Sulfasalazine, Tenofovir, Tenofovir disoproxil fumarate, Triclabendazole, Trimethoprim, Valganciclovir, Valproic acid, Velpatasvir, Sodium valproate, Voriconazole and Zidovudine.

Examples of medicinal components for which the maximum blend amount per tablet exceeds 10 mg but is not more than 100 mg include Aripiprazole, Artesunate, Ascorbic acid, Azathioprine, Bazedoxifene acetate, Bicalutamide, Calcium folinate, Clomifene, Cyclizine, Cyclophosphamide, Dasatinib hydrate, Delamanid, Dolutegravir, Eletriptan hydrobromide, Febuxostat, Fluoxetine, Furosemide, Galantamine Hydrobromide, Hydralazine, Hydrochlorothiazide, Hydrocortisone, Memantine Hydrochloride, Mercaptopurine, Midazolam, Miltefosine, Minodronic Acid Hydrate, Mirtazapine, Neostigmine, Nicotineamide, Olmesartan Medoxomil, Omeprazole, Ondansetron, Pancrelipase, Potassium iodine, Prednisolone, Primaquine, Primethamine, Propranolol, Propylthiouracil, Pyridoxine, Simvastatin, Sitafloxacin hydrate, Spironolactone, Tadalafil, Tamoxifen, Thiamine, Tioguanine, Tolvaptan, Ulipristal, Vardenafil Hydrochloride Hydrate, Zinc sulfate, Acotiamide hydrochloride hydrate, Amitriptyline, Bedaquline, Benznidazole, Bosentan hydrate, Chlorpromazine, Cinacalcet hydrochloride, Daclatasvir, Dapsone, Diethylcarbamazine, Doxycycline, Entacapone, Eplerenone, Ferrous sulfate, Gliclazide, Ibandronate Sodium Hydrate, Losartan, Miglitol, Nitrofurantoin, Phenobarbital, Phenytoin, Pyridostigmine, Raloxifene Hydrochloride, Ritonavir, Succimer, Telmisartan, Topiramate and Verapamil.

Examples of medicinal components for which the maximum blend amount per tablet is not more than 10 mg include Anastrozole, Dienogest, Digoxin, Dutasteride, Entecavir, Entecavir hydrate, Ethinylestradiol, Finasteride, Fludrocorti sone, Glyceryl trinitrate, lmidafenacin, Levothyroxine, Levonorgestrel, Misoprostol, Repaglinide, Ambrisentan, Amiloride, Amlodipine, Bepotastine Besilate, Biperiden, Bisoprolol, Blonanserin, Chlorambucil, Dexamethasone, Diazepam, Enalapril, Ergocalciferol, Escitalopram Oxalate, Esomeprazole magnesium hydrate, Eszopiclone, Ezetimibe, Fludarabine, Fluticasone furoate, Folic acid, Haloperidol, Isosorbide dinitrate, Ivermectin, Lenalidomide hydrate, Levocetirizine hydrochloride, Levonorgestrel, Loperamide, Loratadine, Medroxyprogesterone acetate, Methadone, Methotrexate, Metoclopramide, Mitiglinide Calcium Hydrate, Montelukast Sodium, Norethisterone, Paliperidone, Phytomenadione or Phytonadione, Ramelteon, Riboflavin, Risperidone, Rizatriptan benzoate, Ropinirole hydrochloride, Rosuvastatin Calcium, Senna, Silodosin, Solifenacin succinate and Warfarin.

These active components and medicinal components may be blended in a finely ground state, together with the cellulose composition of an embodiment of the present invention, into the tablet mixture. For example, the active component used in the present invention may be finely ground to an average particle size of at least 1 μm but not more than 40 μm for purposes such as improving the dispersibility of the active component or improving the mixing uniformity of an active component having a medicinal effect at very small amounts. The average particle size of the active component is more preferably at least 1 μm but not more than 20 μm, and even more preferably at least 1 μm but not more than 10 μm.

The blend proportion of the above active component relative to the tablet mixture, expressed relative to the total mass of the obtained tablet, is typically less than 50% by mass, and is preferably not more than 40% by mass, more preferably not more than 30% by mass, even more preferably not more than 20% by mass, and particularly preferably 10% by mass or less. A lower limit of 0.01% by mass is practically applicable. If the proportion of the active component is less than 50% by mass, then maldistribution tends to occur more easily, requiring an accompanying lengthening of the mixing time. However, by using the cellulose composition of an embodiment of the present invention, because any reduction in the tablet hardness caused by lengthening of the mixing time can be effectively suppressed, the cellulose composition of an embodiment of the present invention exhibits particularly marked effects when used in tablets for which the active component content falls within the range described above.

[Lubricant]

The tablet mixture preferably contains a lubricant in addition to the active component described above.

One or more compounds selected from the group consisting of fatty acid metal salts, fatty acid esters and fatty acid ester metal salts may be used as the lubricant, and specific examples include those compounds classified as lubricants in “Pharmaceutical Excipients Directory 2016” (published by Yakuji Nippo, Ltd.), such as magnesium stearate, calcium stearate, stearic acid, sucrose fatty acid esters, and talc. One compound selected from among the above lubricants may be used alone, or a combination of two or more lubricants may be used.

The blend proportion of the above lubricant in the tablet mixture, expressed relative to the total mass of the obtained tablet, is typically at least 0.3% by mass but not more than 5% by mass, and preferably at least 0.5% by mass but not more than 3% by mass.

[Other Additives]

The tablet mixture may also contain other additives in addition to the active component described above.

Examples of these other additives include excipients, disintegrants, binders, fluidizing agents, flavorings, fragrances, colorants and sweeteners.

Examples of excipients other than the cellulose composition include those substances classified as excipients in “Pharmaceutical Excipients Directory 2016” (published by Yakuji Nippo, Ltd.), such as starch acrylate, L-aspartic acid, aminoethylsulfonic acid, aminoacetic acid, corn syrup (powder), gum arabic, gum arabic powder, alginic acid, sodium alginate, pregelatinized starch, pumice particles, inositol, ethylcellulose, ethylene-vinyl acetate copolymer, sodium chloride, olive oil, kaolin, cacao butter, casein, fructose, pumice particles, carmellose, carmellose sodium, hydrated silicone dioxide, dried yeast, dried aluminum hydroxide gel, dried sodium sulfate, dried magnesium sulfate, agar, agar powder, xylitol, citric acid, sodium citrate, disodium citrate, glycerol, calcium glycerophosphate, sodium gluconate, L-glutamine, clay, clay 3, clay particles, croscarmellose sodium, crospovidone, magnesium aluminosilicate, calcium silicate, magnesium silicate, light anhydrous silicate, light liquid paraffin, cinnamon powder, crystalline cellulose, crystalline cellulose carmellose sodium, crystalline cellulose (particles), brown rice koji, synthetic aluminum silicate, synthetic hydrotalcite, sesame oil, wheat flour, wheat starch, wheat germ flour, rice flour, rice starch, potassium acetate, calcium acetate, cellulose acetate phthalate, safflower oil, white beeswax, zinc oxide, titanium oxide, magnesium oxide, β-cyclodextrin, dihydroxyaluminum aminoacetate, 2,6-di-butyl-4-methylphenol, di methylpolysiloxane, tartaric acid, potassium hydrogen tartrate, calcined gypsum, sucrose fatty acid ester, magnesium aluminum hydroxide, aluminum hydroxide gel, co-precipitates of aluminum hydroxide and sodium hydrogen carbonate, magnesium hydroxide, squalane, stearyl alcohol, stearic acid, calcium stearate, polyoxyl stearate, magnesium stearate, hardened soybean oil, purified gelatin, purified shellac, purified white sugar, purified white sugar granules, cetostearyl alcohol, polyethylene glycol 1000 monocetyl ether, gelatin, sorbitan fatty acid ester, D-sorbitol, tribasic calcium phosphate, soybean oil, unsaponified soybean, soybean lecithin, defatted milk powder, talc, ammonium carbonate, calcium carbonate, magnesium carbonate, neutral anhydrous sodium sulfate, low-substituted hydroxypropyl cellulose, dextran, dextrin, natural aluminum silicate, corn starch, tragacanth powder, silicon dioxide, calcium lactate, lactose, lactose granules, Perfiller 101, white shellac, white vaseline, white clay, white sugar, white sugar-starch granules, rye green leaf extract powder, dried powder of rye bud juice, honey, paraffin, potato starch, semi-digested starch, human serum albumin, hydroxypropyl starch, hydroxypropyl cellulose, hydroxypropyl methylcellulose phthalate, phytic acid, glucose, glucose hydrate, partially pregelatinized starch, pullulan, propylene glycol, reduced maltose starch syrup powder, powdered cellulose, pectin, bentonite, sodium polyacrylate, polyoxyethylene alkyl ether, polyoxyethylene hardened castor oil, polyoxyethylene (105) polyoxypropylene (5) glycol, polyoxyethylene (160) polyoxypropylene (30) glycol, sodium polystyrenesulfonate, polysorbate 80, polyvinylacetal diethylamino acetate, polyvinyl pyrrolidone, polyethylene glycol, maltitol, maltose, D-mannitol, starch syrup, isopropyl myristate, anhydrous lactose, anhydrous calcium hydrogen phosphate, anhydrous calcium phosphate granules, magnesium aluminometasilicate, methylcellulose, cotton seed powder, cotton seed oil, wood wax, aluminum monostearate, glycerol monostearate, sorbitan monostearate, medical charcoal, peanut oil, aluminum sulfate, calcium sulfate, granular corn starch, liquid paraffin, dl-malic acid, calcium monohydrogen phosphate, calcium hydrogen phosphate, calcium hydrogen phosphate granules, sodium hydrogen phosphate, potassium dihydrogen phosphate, calcium dihydrogen phosphate and sodium dihydrogen phosphate. One of these excipients may be used alone, or a combination of two or more excipients may be used.

Examples of disintegrants include those substances classified as disintegrants in "Pharmaceutical Excipients Directory 2016" (published by Yakuji Nippo, Ltd.), including celluloses such as croscarmellose sodium, carmellose, carmellose calcium, carmellose sodium and low-substituted hydroxypropyl cellulose; starches such as sodium carboxymethyl starch, hydroxypropyl starch, rice starch, wheat starch, corn starch, potato starch and partially pregelatinized starch; and synthetic polymers such as crospovidone and crospovidone copolymers. One substance selected from among the above disintegrants may be used alone, or a combination of two or more disintegrants may be used.

Examples of binders include those substances classified as binders in "Pharmaceutical Excipients Directory 2016" (published by Yakuji Nippo, Ltd.), including sugars such as white sugar, glucose, lactose and fructose; sugar alcohols such as mannitol, xylitol, maltitol, erythritol and sorbitol; water-soluble polysaccharides such as gelatin, pullulan, carrageenan, locust bean gum, agar, glucomannan, xanthan gum, tamarind gum, pectin, sodium alginate and gum arabic; celluloses such as crystalline cellulose, powdered cellulose, hydroxypropyl cellulose and methylcellulose; starches such as pregelatinized starch and starch paste; synthetic polymers such as polyvinylpyrrolidone, carboxyvinyl polymer and polyvinyl alcohol; and inorganic compounds such as calcium hydrogen phosphate, calcium carbonate, synthetic hydrotalcite and magnesium aluminosilicate. One substance selected from among the above binders may be used alone, or a combination of two or more binders may be used.

Examples of fluidizing agents include those substances classified as fluidizing agents in "Pharmaceutical Excipients Directory 2016" (published by Yakuji Nippo, Ltd.), including silicon compounds such as hydrated silicon dioxide and light anhydrous silicate. One substance selected from among the above fluidizing agents may be used alone, or a combination of two or more fluidizing agents may be used.

Examples of flavorings include those substances classified as flavorings in "Pharmaceutical Excipients Directory 2016" (published by Yakuji Nippo, Ltd.), such as glutamic acid, fumaric acid, succinic acid, citric acid, sodium citrate, tartaric acid, malic acid, ascorbic acid, sodium chloride and 1-menthol. One substance selected from among the above flavorings may be used alone, or a combination of two or more flavorings may be used.

Examples of fragrances include those substances classified as fragrances in "Pharmaceutical Excipients Directory 2016" (published by Yakuji Nippo, Ltd.), including oils such as orange, vanilla, strawberry, yogurt, menthol, fennel oil, cinnamon oil, picea oil and peppermint oil, and green tea powder. One substance selected from among the above fragrances may be used alone, or a combination of two or more fragrances may be used.

Examples of colorants include those substances classified as colorants in "Pharmaceutical Excipients Directory 2016" (published by Yakuji Nippo, Ltd.), including food dyes such as food red No. 3, food yellow No. 5 and food blue No. 1, as well as sodium copper chlorophyllin, titanium oxide and riboflavin. One substance selected from among the above colorants may be used alone, or a combination of two or more colorants may be used.

Examples of sweeteners include those substances classified as sweeteners in "Pharmaceutical Excipients Directory 2016" (published by Yakuji Nippo, Ltd.), such as aspartame, saccharin, dipotassium glycyrrhizinate, stevia, maltose, maltitol, starch syrup and sweet hydrangea leaf powder. One substance selected from among the above sweeteners may be used alone, or a combination of two or more sweeteners may be used.

<Method for Producing Tablet>

A method for producing a tablet by compressing the above tablet mixture (a method for producing a tablet according to an embodiment of the present invention) is described below in detail, but this method is merely one example, and the effects of embodiments of the present invention are not limited to the method described below.

A method in which the active component and the cellulose composition of an embodiment of the present invention are mixed together and then subjected to compression molding may be used as the method for producing a tablet. During this process, besides the active component, other additives may also be blended into the mixture according to need. Examples of these additives include one or more components selected from among components such as the lubricants, excipients, disintegrants, binders, fluidizing agents, flavorings, fragrances, colorants, sweeteners and solubilizers described above.

There are no particular limitations on the order in which the various components are added, and any one of (i) a method in which the active component, the cellulose composition of an embodiment of the present invention, and any other additives that are required are mixed in a single batch, and the resulting mixture is then subjected to compression molding, (ii) a method in which the active component and certain optional additives are premixed, the resulting premixture is then mixed with the cellulose composition of an embodiment of the present invention and other optional additives, and the resulting mixture is then subjected to compression molding, and (iii) a method in which the active component, the cellulose composition of an embodiment of the present invention, and other additives that are required are premixed, the resulting premixture is then mixed with other additives as required, and the obtained mixture is then subjected to compression molding. The method (i) is preferred from the viewpoint of operational simplicity. There are no particular limitations on the method used for adding each of the components, and any typically used method may be employed to add the components either continuously or in batches, using a small suction transport device, air transport device, bucket conveyer, pressure-fed transport device, vacuum conveyer, quantitative vibration feeder, sprayer, or funnel or the like. Examples of spraying methods that may be used include methods for spraying a solution or dispersion of the active component using a pressure nozzle, two-fluid nozzle, four-fluid nozzle, rotating disk, or ultrasonic nozzle or the like, and methods for dripping a solution or dispersion of the active component from a tube-like nozzle.

There are no particular limitations on the mixing method, and any typically used method may be employed, using a rotating vessel mixer such as a V-type mixer, W-type mixer, double cone type mixer or container tack mixer; a stirring mixer such as a high-speed stirring mixer, universal stirring mixer, ribbon mixer, pug mixer, or nauta mixer; or a super mixer, a drum mixer, or a fluidized bed mixer or the like. Further, a shaken vessel mixer such as a shaker or the like may also be used.

There are no particular limitations on the compression molding method used on the composition, and any typically used method may be employed, including methods that use a mortar and pestle to achieve compression molding into the desired shape, and methods in which the composition is first compression molded into sheet form, and the sheet is then cut into the desired shape. Examples of compression molding devices that may be used include roller-type presses such as a hydrostatic press, a briquetting roller press, or a smooth roller press, and compressors such as a single-punch tableting machine or a rotary tableting machine.

There are no particular limitations on the method used for dissolving or dispersing the active component in a medium, and typically used dissolution or dispersion methods may be used, including stirred mixing methods using a stirring blade such as a one-way rotational blade, multi-shaft rotating blade, reciprocating and reversing blade, vertically moving blade, rotating and vertically moving blade or tube-like blade, such as a portable mixer, spatial mixer or side surface mixer, jet-type stirred mixing methods such as a line mixer, gas blowing stirred mixing methods, mixing methods using a high-shear homogenizer, high-pressure homogenizer, or ultrasonic homogenizer, or the like, and shaken vessel mixing methods using a shaker.

There are no particular limitations on the solvent used in the production method described above, provided the solvent is suitable for use in pharmaceuticals, and for example, at least one of water and an organic solvent may be used. Examples of organic solvents include those compounds classified as solvents in "Pharmaceutical Excipients Directory 2016" (published by Yakuji Nippo, Ltd.), including alcohols such as methanol, ethanol, isopropyl alcohol, butyl alcohol, 2-methylbutyl alcohol and benzyl alcohol; hydrocarbons such as pentane, hexane, heptane and cyclohexane; and ketones such as acetone and ethyl methyl ketone. One of these solvents may be used alone, a combination of two or more solvents may be used, or initial dispersion may be performed in one solvent, and that solvent may then be removed and the product dispersed in a different solvent.

When dissolving the active component in a medium, a water-soluble polymer, oil or fat, or surfactant or the like may be used as a solubilizer. Examples of water-soluble polymers, oils and fats, and surfactants that may be used as solubilizers include those substances disclosed in "Pharmaceutical Excipients Directory 2016" (published by Yakuji Nippo, Ltd.). One of these solubilizers may be used alone, or a combination of two or more solubilizers may be used.

In this description, the term "molded body" refers to a body in the form of a granule, fine grain, slug, or tablet or the like, containing the cellulose composition of an embodiment of the present invention, at least one active component, and other additives as required.

Examples of the method used for molding tablets include direct tableting methods in which a mixture prepared by mixing at least one active component and the cellulose composition of an embodiment of the present invention, or a mixture prepared by mixing at least one active component, the cellulose composition of an embodiment of the present invention and other additives as required is subjected to compression molding. Other production methods may also be used, including a production method for polynuclear tablets in which a tablet that has undergone compression molding in advance is used as an inner nucleus, and a production method for multi-layer tablets in which a plurality of pre-compressed molded bodies are stacked together and recompressed. The direct tableting method is preferred from the viewpoints of productivity and ease of process control.

The compression molded tablet (molded body) may be subjected to additional coating. Examples of coating agents that may be used in such cases include the coating agents disclosed in "Pharmaceutical Excipients Directory 2016" (published by Yakuji Nippo, Ltd.). One of these coating agents may be used alone, or a combination of two or more coating agents may be used.

In those cases the production process includes a granulation step, examples of the granulation method include dry granulation, wet granulation, heat granulation, spray granulation and microencapsulation. More specifically, among the various wet granulation methods, fluidized bed granulation, stirring granulation, extrusion granulation, crushing granulation and rolling granulation are effective. In the fluidized bed granulation method, the granulation is performed in a fluidized bed granulation device by spraying a binder solution onto the fluidized powder. In the stirring granulation method, mixing, kneading and granulation of the powder are conducted simultaneously in a sealed structure by rotating a stirring blade inside a mixing tank while a binding solution is added. In the extrusion granulation method, granulation is performed by forcefully extruding a wet mass which has been kneaded by adding a binder solution through a screen of a suitable size using a screw method or basket method. In the crushing granulation method, granulation is performed by shearing and crushing a wet mass which has been kneaded by adding a binder solution using the rotating blade of a granulator, and the resulting centrifugal force forces the crushed wet mass through an outer peripheral screen. In the rolling granulation method, spherical granules are rolled by the centrifugal force of a rotating rotor while a binder solution is sprayed from a spray gun, thereby growing spherical granules having uniform particle size in a snowball-like manner.

The method used for drying the granules may employ any of various methods, including hot air heating (shelf drying, vacuum drying, fluidized bed drying), conduction heat transfer (flat pan drying, shelf box drying, drum drying), and freeze drying. In hot air heating, hot air is brought into direct contact with the additive, and the evaporated water is removed at the same time. In conduction heat transfer, the additive is heated indirectly through a heat transfer wall. In freeze drying, the additive is frozen at a temperature of at least −10° C. but not more than 40° C., and water is then removed by sublimation by heating under high vacuum (of at least $1.3\times10^{-5}$ MPa but not higher than $2.6\times10^{-4}$ MPa).

EXAMPLES

Embodiments of the present invention are described below in further detail using a series of examples and comparative examples, but embodiments of the present invention are not limited to these examples. The various physical properties described in the examples and comparative examples and the methods used for measuring those properties are as described below. In those cases where a sample contained a large amount of water, the sample was subjected to preliminary drying to reduce the water content to at least 3.5% by mass but not more than about 4.5% by mass prior to conducting measurement of the various physical properties.

<Method for Analyzing Cellulose Compositions>

[Analysis 1]

(Method for Measuring Water-Soluble Substance Content in Cellulose Composition)

The water-soluble substance content in the cellulose composition was measured in accordance with the crystalline cellulose purity test (2) method described in the 17th edition of the Japanese Pharmacopoeia.

Specifically, 80 mL of purified water was added to 5.0 g of the cellulose composition, and the mixture was shaken and mixed for 10 minutes. Subsequently, the cellulose composition-containing solution was suction-filtered using a filter paper for quantitative analysis (Type 5C). The filtrate was evaporated to dryness without charring in a beaker of known mass, subsequently dried at 105° C. for one hour, and then left to cool in a desiccator to obtain a residue. The mass of the thus obtained residue was then weighed to determine the mass of the residue. Each powder was measured twice and the average value was used. Further, a blank test was also conducted via the above operations using only 80 mL of purified water, without adding 5.0 g of the cellulose composition, and the water-soluble substance content detected in the blank test was subtracted from the measured value to obtain a value. This value was rounded to the second decimal place to obtain a measured value for the water-soluble substance content. The water-soluble substance content determined by this test method represents the amount of water-soluble substances contained in 5 g of the cellulose composition.

[Analysis 2]

(Method for Measuring Cellooligosaccharide (3 to 7) Content)

The total mass of dried solid of water-soluble substances obtained in the above "Analysis 1" was redissolved in 10 mL of a 50% (v/v) aqueous solution of acetonitrile, the resulting solution was filtered through a filter (0.20 μm), and LC/MS was then used to measure the cellooligosaccharide (3 to 7) content.

A precision balance was used during preparation and dilution of the measurement solution, and the measured weight was used to determine the sample concentration and dilution ratio.

Further, for the measurement of the cellooligosaccharide content, solutions of known concentrations prepared using commercially available products of cellotriose (trisaccharide), cellotetraose (tetrasaccharide) and cellopentaose (pentasaccharide) were analyzed by LC/MS, the retention time and m/z ion chromatogram peak surface area for each cellooligosaccharide were determined, and calibration curves (sample concentration vs. peak surface area) were produced. Using these calibration curves, the amount of each cellooligosaccharide in the water-soluble substances (of 5 g of the cellulose composition) was determined.

The amounts of cellohexaose (hexasaccharide) and celloheptaose (heptasaccharide), for which commercially available products are unavailable, were determined by the following calculation method using the trends observed in peak surface area when previously measured glucose (monosaccharide) to cellopentaose (pentasaccharide) solutions were analyzed at the same concentrations. The total amount of each oligosaccharide was recorded as a value rounded to the second decimal place.

(Calculation Method)

Cellohexaose (hexasaccharide): Using the calibration curve for cellopentaose (pentasaccharide), the peak surface area was substituted with the peak surface area for cellohexaose (hexasaccharide), and the thus obtained cellooligosaccharide content was multiplied by a correction coefficient (0.729) to calculate the amount of cellohexaose (hexasaccharide).

Celloheptaose (heptasaccharide): Using the calibration curve for cellopentaose (pentasaccharide), the peak surface area was substituted with the peak surface area for celloheptaose (heptasaccharide), and the thus obtained cellooligosaccharide content was multiplied by a correction coefficient (0.531) to calculate the amount of celloheptaose (heptasaccharide).

The LC/MS measurements were conducted in accordance with the measurement conditions listed below. If measurements are conducted with a portion of the following conditions altered, then the cellooligosaccharide calibration curves described above must be reproduced in accordance with the altered conditions.

(Measurement Conditions)

LC apparatus: Nexera, manufactured by Shimadzu Corporation

Column: Asahipak NH2P-50 2D (2 mm I.D.×150 mm), manufactured by Shodex K.K.

Column temperature: 40° C.

Detector: PDA detector 200 to 400 nm

Flow rate: 0.3 mL/min

Mobile phase: A=purified water, B=acetonitrile

Gradient: gradient conditions are shown below in Table 1

Injection volume: 10 μL

MS apparatus: Synapt G2, manufactured by Waters Corporation

Ionization conditions: $ESU^-$

Scan range: m/z 50 to 2,000

TABLE 1

| Time (min) | A (%) | B (%) |
|---|---|---|
| 0 | 10 | 90 |
| 15 | 50 | 50 |
| 15.1 | 10 | 90 |
| 25 | 10 | 90 |

For reference purposes, the detected ion (m/z) and retention time for each structural component observed under the measurement conditions described above are shown below in Table 2.

TABLE 2

| | | Detected ion m/z | Retention time (min) |
|---|---|---|---|
| Cellotriose | trisaccharide | 549.17 [M + HCOO]⁻ | 9.2 |
| Cellotetraose | tetrasaccharide | 711.22 [M + HCOO]⁻ | 10.3 |
| Cellopentaose | pentasaccharide | 873.28 [M + HCOO]⁻ | 11.2 |
| Cellohexaose | hexasaccharide | 989.32 [M − H]⁻ | 11.9 |
| Celloheptaose | heptasaccharide | 1151.38 [M − H]⁻ | 12.5 |

<Methods for Measuring Powder Physical Properties>

Methods for measuring the powder physical properties in those cases where the cellulose composition is a cellulose powder are described below.

[Physical Property 1]

(Average Particle Size)

Using a laser diffraction particle size distribution meter (LA-950 V2 (brand name), manufactured by Horiba, Ltd.), measurement was conducted in the dry measurement mode at a compressed air pressure of 0.10 MPa, a feeder speed of 160, a feeder initial speed coefficient of 1.2, and a refractive index of 1.51. The particle size at a cumulative volume of 50% in the distribution obtained from the measurement was deemed the average particle size (μm) of the cellulose powder.

[Physical Property 2]

(Loose Bulk Density)

For this measurement, a cellulose powder for which the water content had been adjusted to a value of at least 3.5% by mass but not more than 4.5% by mass was used. In those cases where the water content of the cellulose powder was lower than this range, the water content of the cellulose powder was adjusted by allowing the powder to absorb moisture in a constant temperature and humidity chamber or the like. In those cases where the water content exceeded the above range, the water content was adjusted to a value within the range by blowing hot air at 60° C. evenly onto the cellulose powder in a hot air oven.

Subsequently, a Scott Volumeter (model ASTM B-329-85, manufactured by Tsutsui Rikagaku Kikai) was used to measure the loose bulk density of the cellulose powder, by passing the cellulose powder through a sieve (mesh size: 1 mm) and filling a 25 mL cylindrical metal container. The powder at the top of the 25 mL cylindrical metal container containing the cellulose powder was leveled off, and the mass (g) of the cellulose powder inside the container was divided by 25 mL to determine the loose bulk density (g/mL). The measurement was conducted 5 times and the average value was determined.

[Physical Property 3]

(Packed Bulk Density)

For this measurement, a cellulose powder for which the water content had been adjusted to a value of at least 3.5% by mass but not more than 4.5% by mass was used. The water content was adjusted to a value within this range using the methods described above in "Physical Property 2". The packed bulk density (packed apparent specific gravity) (g/mL) was calculated using a powder physical property tester (PT-R, manufactured by Hosokawa Micron Corporation). The sieve used had a mesh size of 710 μm, and the funnel used was made of metal (coated with an antistatic spray) and had an inner diameter of 0.8 cm. Testing was conducted with Vibration set to 2.0 (power supply: AC 100V, 60 Hz).

[Physical Property 4]

(Compressibility)

The compressibility of each cellulose powder was calculated using the following formula.

$$\text{Compressibility (\%)} = ([\text{packed bulk density}] - [\text{loose bulk density}]) / [\text{packed bulk density}] \times 100$$

[Physical Property 5]

(Primary Particle-Equivalent Particle Size)

First, 0.5 g of the cellulose powder was placed in 10 mL of pure water, and following ultrasonic irradiation (600 W, 40 kHz) for 10 minutes, a laser diffraction particle size distribution meter (LA-950 V2 (brand name), manufactured by Horiba, Ltd.) was used to conduct measurement in the wet measurement mode under conditions including a refractive index of 1.20 (cellulose refractive index: 1.59, water refractive index: 1.33), pretreatment conditions (ultrasonic irradiation: 1 minute, ultrasonic wave intensity: 1), a circulation speed of 7, and a stirring speed of 5. The particle size at a cumulative volume of 50% in the distribution obtained from the measurement was deemed the cellulose primary particle-equivalent average particle size (primary particle-equivalent particle size) (μm).

[Physical Property 6]

(Ratio L/D of Long Axis to Short Axis for Cellulose Particles)

The cellulose powder was dispersed on a glass plate and an image was acquired with a microscope (VHX-1000, manufactured by Keyence Corporation) at a magnification of 500×. The captured image was analyzed with image processing analysis system software (Image Hyper II, manufactured by DigiMo Ltd.) using the procedures described below, and the aspect ratio of the particles (the ratio of the long axis to the short axis; L/D) was measured. Measurements were conducted for at least 50 particles, and the average value was determined.

(1) Procedure 1: Binarization Processing

The image captured by the microscope was imported as a monochrome image into analysis software, and the scale of the image was set using the distance between two points method. Next, the "Otsu method" was selected for the binarization process, and the threshold value was set. Because the optimum threshold value differs for each image, the threshold value was selected by comparison with the original image to ensure the best possible match with the shape of the original particle.

(2) Procedure 2: Binarization with Manual Correction

By comparison with the originally acquired image, particles for which a suitable measurement result could not be obtained, such as overlapping particles, particles protruding beyond the image edges, and particles with indistinct or blurred outlines were deleted and removed from the measurement target image.

(3) Procedure (3): Hole Filling

Hole filling was conducted using the "hole filling" mode with a value of "8" was selected for the "neighborhood" setting. Subsequently, a second comparison with the original image was conducted by "binarization with manual correction", and a confirmation was made as to whether the correction was able to be conducted normally. When normal correction could not be achieved, another manual correction was conducted.

(4) Procedure 4: Image Measurement

The number of deleted pixels was set to "100" and the "neighborhood" was set to "8", and "image measurement" was then executed. The measurement results for the "long axis" and the "short axis" for each measured particle are displayed on a computer. The numerical value obtained by dividing the "long axis" by the "short axis" was used as the aspect ratio.

<Tablet Evaluation Methods>

Tablets were produced and subjected to a number of evaluations using the methods described below.

[Preparation of Tableting Powder]

The blend raw materials described below (excluding the magnesium stearate lubricant) were placed in a V-type mixer (V-5, manufactured by Tokuju Corporation) and mixed for 60 minutes.

TABLE 3

| | Blend 1 | Blend 2 | Blend 3 | Blend 4 |
|---|---|---|---|---|
| Chlorpheniramine d-maleate | 20 g | — | 20 g | 20 g |
| Folic acid | — | 4 g | — | — |
| Cellulose composition | 200 g | 200 g | 200 g | 200 g |
| Mannitol | 1760 g | 1776 g | 1720 g | 1770 g |
| Magnesium stearate | 20 g | 20 g | 60 g | 10 g |

Subsequently, the magnesium stearate was added as a lubricant, and mixing was conducted for either 5 minutes or 30 minutes to obtain a tableting powder (mixing time: 5 minutes or 30 minutes).

[Production of Tablets]

The tableting powder (mixing time: 5 minutes or 30 minutes) was tableted for 10 minutes using a rotary tableting machine (Clean Press Correct 12HUK, manufactured by Kikusui Seisakusho Ltd., 12 stations, turntable: 54 rpm, open feeder, applied pressure: 7 kN), thus obtaining 200 mg 08 mm-12R tablets.

[Evaluation 1]

(Tablet Hardness and Tablet Hardness Reduction Rate)

The tablets for measuring hardness were tablets sampled within the 30 seconds immediately prior to stopping operation of the rotary tableting machine. The hardness of each tablet was measured at least 20 hours but not more than 48 hours after tableting using a hardness meter (Dr. Schleuniger Tablet Tester 8M). The average value for 10 tablets at each tableting pressure was deemed the tablet hardness. Tablets for which the tablet hardness was at least 55 N were deemed favorable.

Further, the tablet hardness reduction rate was determined using the following formula, based on the difference between the hardness (N1) of tablets produced from the tableting powder (mixing time: 5 minutes) and the hardness (N2) of tablets produced from the tableting powder (mixing time: 30 minutes).

$$\text{Tablet Hardness Reduction Rate (\%)} = (1 - N2/N1) \times 100$$

(Active Component Content CV Value)

First, a calibration curve was produced for the active component. Specifically, the absorption spectrum of the active component was measured using an absorption spectrometer, and a calibration curve was produced based on the peak top wavelength (for example, chlorpheniramine d-maleate: 264 nm, folic acid: 290 nm).

The tablets for measuring the active component content CV value were tablets sampled within the 30 seconds immediately prior to stopping operation of the tableting machine. A single tablet was weighed, and then placed in a 100 mL measuring flask, which was subsequently filled to 100 mL with pure water. The resulting aqueous solution was filtered through a resin filter to remove the insoluble fraction, and the amount of the active component in the filtrate was quantified by absorptiometry. The active component content in the single tablet was calculated. In the case of tablets, a total of ten tablets were measured, and the average value and standard deviation for the active component content were determined.

Subsequently, using the formula below, the coefficient of variation (also referred to as the "active component content CV value") which acts as a measure of the uniformity was determined. A lower coefficient of variation was evaluated as indicating favorable uniformity in the active component content.

$$\text{Active component content } CV \text{ value (\%)} = ([\text{standard deviation}]/[\text{average value for active component content}]) \times 100$$

(Tableting Failure)

In the "Production of Tablets" described above, the lower pestles of the rotary tableting machine were inspected visually after the 10-minute tableting operation, and the level of pestle clouding (powder adhesion) was evaluated. The evaluation criteria used were as follows.

(Evaluation Criteria)

○: no powder adhesion

Δ: a thin layer of powder adhesion, producing a slightly clouded state (with no metallic luster visible on the pestle surface)

×: adhesion of powder clearly visible

[Evaluation 4]

(Storage Stability (Cellulose Composition and Active Component Reactivity Evaluation))

Using aminophylline as the active component, the reactivity with the cellulose composition was evaluated in the manner described below.

First, a powder prepared by mixing the cellulose composition and aminophylline in a ratio of 1:1 (parts by mass) in a plastic bag was tableted in a static pressure tableting machine (applied pressure: 7 kN, holding time: 10 seconds), thus forming Ø11.3 mm 500 mg flat tablets.

Immediately following tableting, a tablet obtained using the above production method was analyzed using a spectroscopic colorimeter (SE-2000, manufactured by Nippon Denshoku Industries Co., Ltd.) to determine values for the lightness (L), the saturation (green to red) (a), and the saturation (blue to yellow) (b). The whiteness was then calculated using the following formula.

$$\text{Whiteness} = 100 - \left[(100 - L)^2 + a^2 + b^2\right]^{0.5}$$

Further, a tableted tablet was placed in a glass bottle, the bottle was sealed and stored for one month in a constant temperature and humidity chamber set to a temperature of 40° C. and a humidity of 75% RH, and then following storage, the L, a and b values were remeasured using the spectroscopic colorimeter, and the above formula was used to calculate the whiteness following the storage stability test.

The change in whiteness between immediately following tableting (before storage) and following the storage stability test (after storage) was calculated using the formula shown below, and this change in whiteness was deemed to indicate the reactivity between the cellulose composition and the active component.

$$\text{Change in whiteness} = \text{whiteness (before storage)} - \text{whiteness (after storage)}$$

If the absolute value of the change in whiteness exceeds 10%, then the color change is discernible even visually, and therefore tablets for which the absolute value of the change in whiteness was 10% or less were evaluated as having favorable storage stability.

<Preparation of Wet Floc>

Preparation Example 1

(Preparation of Wet Floc X)

Two kg of shredded commercially available pulp and 30 L of an aqueous solution of hydrochloric acid were placed in a low-speed stirrer (30 LGL reactor (trade name) manufactured by Ikebukuro Horo Kogyo Co., Ltd.) and hydrolyzed under stirring (reaction conditions: hydrochloric acid concentration of 0.5%, reaction temperature of 120° C., reaction time of 1.0 hours, and stirring speed of 220 rpm), thus obtaining an acid-insoluble residue. The obtained acid-insoluble residue was washed thoroughly with pure water until the electrical conductivity of the filtrate fell to less than 100 μS/cm, and then filtered to obtain a wet floc X. Measurement of the average degree of polymerization of the wet floc X using the copper ethylenediamine solution viscosity method disclosed in confirmation test (3) for crystalline cellulose in the Japanese Pharmacopoeia revealed an average degree of polymerization of 170.

<Preparation of Cellooligosaccharide Extract>

In the preparation of the wet floc X, the filtrate from the hydrolysis reaction that was separated from the acid-insoluble residue was collected. This filtrate was neutralized using a strongly basic anion exchange resin, and then concentrated with an evaporator to precipitate the insoluble matter (cellooligosaccharides). Concentration was continued until the concentrate reached a slurry-like state, at which point concentration was halted before the concentrate dried to form a solid. The thus obtained concentrate was cooled in ice and subjected to suction filtration using a glass filter, and the insoluble matter retained on the glass filter was washed with cold water.

The washed insoluble matter was dried by vacuum drying under reduced pressure, obtaining a cellooligosaccharide extract.

The amount of cellooligosaccharides from trisaccharides to heptasaccharides in the cellooligosaccharide extract was 72% by mass.

<Production of Cellulose Compositions>

Example 1

(Production of Cellulose Powder A)

The wet floc X was introduced into a 90 L plastic bucket, pure water was added to adjust the total solid fraction concentration to 10% by mass, and the mixture was dispersed using a three-one motor to prepare 30 kg of a dispersion. With the dispersion undergoing constant stirring, a neutralization was conducted with aqueous ammonia (pH after neutralization: at least 7.5 but not more than 8.0), 5.56 g of the cellooligosaccharide extract (proportion of trisaccharides to heptasaccharides: 72%) was added and stirred, and the resulting mixture was spray dried (drying conditions: a dispersion supply rate of 6 kg/hour, an inlet temperature at least 180° C. but not more than 220° C., and an outlet temperature at least 50° C. but not more than 70° C.), thus obtaining a cellulose composition A. The water-soluble substance content of the obtained powder was 11.3 mg, the amount of cellooligosaccharides from trisaccharides to heptasaccharides was 7.5 mg, and the proportion of trisaccharides to heptasaccharides within the water-soluble substances was 66% by mass.

Example 2

(Production of Cellulose Powder B)

The wet floc X was introduced into a 90 L plastic bucket, pure water was added to adjust the total solid fraction concentration to 10% by mass, and the mixture was dispersed using a three-one motor to prepare 30 kg of a dispersion. With the dispersion undergoing constant stirring, a neutralization was conducted with aqueous ammonia (pH after neutralization: at least 7.5 but not more than 8.0), 3.39 g of the cellooligosaccharide extract (proportion of trisaccharides to heptasaccharides: 72%) was added and stirred, and the resulting mixture was spray dried (drying conditions: a dispersion supply rate of 6 kg/hour, an inlet temperature at least 180° C. but not more than 220° C., and an outlet temperature at least 50° C. but not more than 70° C.), thus obtaining a cellulose composition B. The water-soluble substance content of the obtained powder was 7.8 mg, the amount of cellooligosaccharides from trisaccharides to heptasaccharides was 5.0 mg, and the proportion of trisaccharides to heptasaccharides within the water-soluble substances was 64% by mass.

Example 3

(Production of Cellulose Powder C)

A high-speed stirring granulator was charged with 800 g of the cellulose composition B obtained in Example 2, and following granulation and subsequent drying in a fluidized bed, the granules were sieved through a 500 μm mesh to obtain a cellulose composition C (granulation conditions: amount of added water 600 g, granulation time 20 minutes, main blade 400 rpm, cross screw 500 rpm; drying conditions: drying temperature 80° C.). The water-soluble substance content of the obtained powder was 7.4 mg, the amount of cellooligosaccharides from trisaccharides to heptasaccharides was 4.7 mg, and the proportion of trisaccharides to heptasaccharides within the water-soluble substances was 64% by mass.

Example 4

(Production of Cellulose Composition D)

The cellulose composition B obtained in Example 2 was ground with a Jet Mill pulverizer to obtain a cellulose composition D. The water-soluble substance content of the obtained powder was 8.9 mg, the amount of cellooligosaccharides from trisaccharides to heptasaccharides was 5.8 mg, and the proportion of trisaccharides to heptasaccharides within the water-soluble substances was 65% by mass.

Example 5

(Production of Cellulose Composition E)

The wet floc X was introduced into a 90 L plastic bucket, pure water was added to adjust the total solid fraction concentration to 10% by mass, and the mixture was dispersed using a three-one motor to prepare 30 kg of a dispersion. With the dispersion undergoing constant stirring, a neutralization was conducted with aqueous ammonia (pH after neutralization: at least 7.5 but not more than 8.0), 2.52 g of the cellooligosaccharide extract (proportion of trisaccharides to heptasaccharides: 72%) was added and stirred, and the resulting mixture was spray dried (drying conditions: a dispersion supply rate of 6 kg/hour, an inlet temperature at least 180° C. but not more than 220° C., and an outlet temperature at least 50° C. but not more than 70° C.), thus obtaining a cellulose composition E. The water-soluble substance content of the obtained powder was 6.4 mg, the amount of cellooligosaccharides from trisaccharides to heptasaccharides was 4.0 mg, and the proportion of trisaccharides to heptasaccharides within the water-soluble substances was 62% by mass.

Comparative Example 1

(Production of Cellulose Composition F)

The wet floc X was introduced into a 90 L plastic bucket, pure water was added to adjust the total solid fraction concentration to 10% by mass, and the mixture was dispersed using a three-one motor to prepare 30 kg of a dispersion. With the dispersion undergoing constant stirring, a neutralization was conducted with aqueous ammonia (pH after neutralization: at least 7.5 but not more than 8.0), and then without adding any cellooligosaccharide extract, the dispersion was spray dried (drying conditions: a dispersion supply rate of 6 kg/hour, an inlet temperature at least 180° C. but not more than 220° C., and an outlet temperature at least 50° C. but not more than 70° C.), thus obtaining a cellulose composition F. The water-soluble substance content of the obtained powder was 2.4 mg, the amount of cellooligosaccharides from trisaccharides to heptasaccharides was 1.1 mg, and the proportion of trisaccharides to heptasaccharides within the water-soluble substances was 46% by mass.

Comparative Example 2

(Production of Cellulose Composition G)

The wet floc X was introduced into a 90 L plastic bucket, pure water was added to adjust the total solid fraction concentration to 10% by mass, and the mixture was dispersed using a three-one motor to prepare 30 kg of a dispersion. With the dispersion undergoing constant stirring, a neutralization was conducted with aqueous ammonia (pH after neutralization: at least 7.5 but not more than 8.0), 7.29 g of the cellooligosaccharide extract (proportion of trisaccharides to heptasaccharides: 72%) was added and stirred, and the resulting mixture was spray dried (drying conditions: a dispersion supply rate of 6 kg/hour, an inlet temperature at least 180° C. but not more than 220° C., and an outlet temperature at least 50° C. but not more than 70° C.), thus obtaining a cellulose composition G. The water-soluble substance content of the obtained powder was 14.1 mg, the amount of cellooligosaccharides from trisaccharides to heptasaccharides was 9.5 mg, and the proportion of trisaccharides to heptasaccharides within the water-soluble substances was 68% by mass.

Using each of the cellulose compositions obtained in the examples and comparative examples, the physical properties were measured using the methods described above, and tablets were produced and subjected to various evaluations. The results of measuring the physical properties are shown in Table 4, and the evaluation results are shown in Table 5. In Table 5, "d-MC" is an abbreviation for chlorpheniramine d-maleate.

TABLE 4

| | | | Example 1 | Example 2 | Example 3 | Example 4 | Example 5 | Comparative Example 1 | Comparative Example 2 |
|---|---|---|---|---|---|---|---|---|---|
| | Cellulose composition | | A | B | C | D | E | F | G |
| Composition | Water-soluble substance content | [mg] | 11.3 | 7.8 | 7.4 | 8.9 | 6.4 | 2.4 | 14.1 |
| | Cellooligosaccharides (3 to 7) content | [mg] | 7.5 | 5.0 | 4.7 | 5.8 | 4.0 | 1.1 | 9.5 |
| | Proportion of cellooligosaccharides (3 to 7) within water-soluble substances | [% by mass] | 66 | 64 | 64 | 65 | 62 | 46 | 68 |

TABLE 4-continued

| | | | Example 1 | Example 2 | Example 3 | Example 4 | Example 5 | Comparative Example 1 | Comparative Example 2 |
|---|---|---|---|---|---|---|---|---|---|
| Physical properties | Average particle size | [μm] | 62 | 59 | 134 | 26 | 56 | 53 | 65 |
| | Loose bulk density | [g/mL] | 0.23 | 0.26 | 0.31 | 0.15 | 0.27 | 0.29 | 0.19 |
| | Packed bulk density | [g/mL] | 0.42 | 0.41 | 0.41 | 0.32 | 0.40 | 0.41 | 0.39 |
| | Compressibility | [—] | 45 | 36 | 25 | 53 | 32 | 30 | 51 |
| | Primary particle-equivalent particle size | [μm] | 24 | 23 | 20 | 24 | 23 | 22 | 23 |
| | L/D | [—] | 2.3 | 2.2 | 1.9 | 2.7 | 2.1 | 2.1 | 2.4 |
| | Reactivity with active component | [%] | −8 | −5 | −4 | −6 | −4 | −3 | −11 |

TABLE 5

| | | | | Example 1 | Example 2 | Example 3 | Example 4 | Example 5 | Comparative Example 1 | Comparative Example 2 |
|---|---|---|---|---|---|---|---|---|---|---|
| Cellulose composition | | | | A | B | C | D | E | F | G |
| Tablet composition | | Blend | | blend 1 | blend 1 | blend 1 | blend 1 | blend 1 | blend 1 | blend 1 |
| | | Active component | | d-MC | d-MC | d-MC | d-MC | d-MC | d-MC | d-MC |
| | | Active component content | [% by mass] | 1 | 1 | 1 | 1 | 1 | 1 | 1 |
| | | Cellulose composition content | [% by mass] | 10 | 10 | 10 | 10 | 10 | 10 | 10 |
| | | Mannitol content | [% by mass] | 88 | 88 | 88 | 88 | 88 | 88 | 88 |
| | | Lubricant content | [% by mass] | 1 | 1 | 1 | 1 | 1 | 1 | 1 |
| Evaluations | 5 minutes | Tablet hardness | [N] | 78 | 67 | 60 | 96 | 65 | 56 | 84 |
| | | Active component content CV value | [% by mass] | 1.9 | 1.7 | 1.3 | 2.0 | 1.6 | 1.5 | 2.5 |
| | | Tableting failure | [—] | ○ | ○ | ○ | ○ | ○ | ○ | ○ |
| | 30 minutes | Tablet hardness | [N] | 75 | 62 | 55 | 90 | 58 | 47 | 82 |
| | | Active component content CV value | [% by mass] | 1.8 | 1.7 | 1.4 | 1.7 | 2.0 | 3.5 | 2.4 |
| | | Tableting failure | [—] | ○ | ○ | ○ | ○ | ○ | ○ | ○ |
| | Tablet hardness reduction rate | | [%] | 3.8 | 7.5 | 8.3 | 6.3 | 10.8 | 16.1 | 2.4 |

From the results in Tables 4 and 5, it is evident that reactivity with the active component was suppressed in the cellulose compositions A to E (Examples 1 to 5), in which the amount of cellooligosaccharides from trisaccharides to heptasaccharides per 5 g of the cellulose composition was at least 4.0 mg but not more than 7.5 mg, and that for the tablets produced using those cellulose compositions, the results for the tablet hardness, the reduction rate in the tablet hardness and the active component content CV value were all favorable, and tableting failure during molding was able to be suppressed.

In contrast, in the case of the cellulose composition F (Comparative Example 1), in which the amount of cellooligosaccharides from trisaccharides to heptasaccharides per 5 g of the cellulose composition was less than 4.0 mg, although reactivity with the active component was low, in the tablets produced using the cellulose composition, tablets having favorable results for the tablet hardness, the reduction rate in the tablet hardness and the active component content CV value could not be obtained.

In the case of the tablets produced using the cellulose composition G (Comparative Example 2), in which the amount of cellooligosaccharides from trisaccharides to heptasaccharides per 5 g of the cellulose composition exceeded 7.5 mg, although the tablet hardness and the reduction rate in the tablet hardness were favorable, the reactivity between the cellulose composition and the active component and the active component content CV value were unsatisfactory.

Examples 6 to 8

Using the cellulose composition B obtained in Example 2, tablets having the blend formulation shown below in Table 6 were produced using the method described above, and then subjected to each of the various evaluations. The results are shown in Table 6. In Table 6, "d-MC" is an abbreviation for chlorpheniramine d-maleate.

TABLE 6

| | | Example 6 | Example 7 | Example 8 |
|---|---|---|---|---|
| Cellulose composition | | B | B | B |
| Tablet composition | Blend | blend 3 | blend 4 | blend 2 |
| | Active component | d-MC | d-MC | folic acid |

TABLE 6-continued

| | | | | Example 6 | Example 7 | Example 8 |
|---|---|---|---|---|---|---|
| | | Active component content | [% by mass] | 1 | 1 | 0.2 |
| | | Cellulose composition content | [% by mass] | 10 | 10 | 10 |
| | | Mannitol content | [% by mass] | 86 | 88.5 | 88.8 |
| | | Lubricant content | [% by mass] | 3 | 0.5 | 1 |
| Evaluations | 5 minutes | Tablet hardness | [N] | 62 | 68 | 66 |
| | | Active component content CV value | [% by mass] | 2.0 | 1.7 | 2.0 |
| | | Tableting failure | [—] | ○ | Δ | ○ |
| | 30 minutes | Tablet hardness | [N] | 57 | 65 | 62 |
| | | Active component content CV value | [% by mass] | 1.7 | 1.7 | 1.9 |
| | | Tableting failure | [—] | ○ | Δ | ○ |
| | Tablet hardness reduction rate | | [%] | 8.1 | 4.4 | 6.1 |

From Table 6, it is evident that in those tablets in which the lubricant content was at least 0.3% by mass but not more than 5% by mass (Examples 6 to 8), the tablet hardness, the reduction rate in the tablet hardness, the active component content CV value, and the tableting failure rate during molding were all favorable.

Furthermore, based on a comparison of tablets that used the cellulose composition B but contained differing amounts of the lubricant (Examples 2, 6 and 7), a tendency was observed for better suppression of tableting failure during molding as the amount of the lubricant was increased.

On the other hand, reducing the amount of the lubricant yielded a tendency for more favorable results for the tablet hardness and the tablet hardness reduction rate.

INDUSTRIAL APPLICABILITY

By using the cellulose composition of an embodiment of the present invention, a cellulose composition can be provided that has favorable hardness and good suppression of both deviation in the active component content and tableting failure during molding. A tablet of an embodiment of the present invention contains the cellulose composition, and exhibits favorable hardness, and good suppression of both deviation in the active component content and tableting failure during molding.

The invention claimed is:

1. A cellulose composition comprising cellulose and a water-soluble substance including cellooligosaccharides from trisaccharides to heptasaccharides, wherein the cellooligosaccharide content per 5 g of the cellulose composition is at least 4.0 mg but not more than 7.5 mg, and wherein the cellulose is in the form of a crystalline cellulose.

2. The cellulose composition according to claim 1, wherein the water-soluble substance content per 5 g of the cellulose composition is at least 2.5 mg but not more than 12.5 mg.

3. The cellulose composition according to claim 2, wherein a proportion of the cellooligosaccharides relative to an entirety of the water-soluble substance is at least 47% by mass but not more than 67% by mass.

4. The cellulose composition according to claim 1, wherein the cellulose composition is a powder, and an average particle size of the powder is at least 10 μm but not more than 200 μm.

5. The cellulose composition according to claim 4, wherein an aspect ratio L/D of the powder is at least 1.8 but not more than 4.0.

6. A tablet comprising the cellulose composition of claim 1, and at least one active component.

7. The tablet according to claim 6, wherein a lubricant content, relative to a total mass of the tablet, is at least 0.3% by mass but not more than 5% by mass.

8. The tablet according to claim 7, wherein the lubricant is at least one substance selected from the group consisting of fatty acid metal salts, fatty acid esters, and fatty acid ester metal salts.

9. The tablet according to claim 7, wherein the lubricant is at least one substance selected from the group consisting of magnesium stearate, calcium stearate, sodium stearyl fumarate, stearic acid, sucrose fatty acid esters, and talc.

10. The tablet according to claim 6, wherein the active component content, relative to a total mass of the tablet, is at least 0.01% by mass and less than 50% by mass.

11. The cellulose composition according to claim 1, wherein the cellulose composition is a powder and each single particle of the powder contains the cellulose and the cellooligosaccharides.

12. The cellulose composition according to claim 1, wherein an average degree of polymerization of the cellulose is 100 to 400.

* * * * *